United States Patent
Hoshi et al.

(10) Patent No.: US 6,967,026 B2
(45) Date of Patent: Nov. 22, 2005

(54) HARD CAPSULE

(75) Inventors: Noboru Hoshi, Iruma (JP); Toshio Shimamoto, Osaka (JP); Shigeru Sugiyama, Osaka (JP)

(73) Assignees: Nisshin Kasei Co., Ltd., Osaka (JP); Daido Chemical Corporation, Osaka (JP)

( * ) Notice: Subject to any disclaimer, the term of this patent is extended or adjusted under 35 U.S.C. 154(b) by 0 days.

(21) Appl. No.: 10/362,114

(22) PCT Filed: Aug. 24, 2001

(86) PCT No.: PCT/JP01/07244

§ 371 (c)(1),
(2), (4) Date: Feb. 19, 2003

(87) PCT Pub. No.: WO02/17848

PCT Pub. Date: Mar. 1, 2002

(65) Prior Publication Data

US 2003/0166763 A1 Sep. 4, 2003

(30) Foreign Application Priority Data

Aug. 29, 2000 (JP) .......................................... 2000-259830

(51) Int. Cl.⁷ ............................ A61J 3/07; C08F 261/04
(52) U.S. Cl. ...................... 424/408; 424/451; 428/35.7; 514/962; 524/459; 526/202
(58) Field of Search ................................ 424/408, 451; 428/35.7; 514/962; 524/459; 526/202

(56) References Cited

U.S. PATENT DOCUMENTS 3,984,494 A * 10/1976 Harreus et al.
5,095,054 A * 3/1992 Lay et al.

FOREIGN PATENT DOCUMENTS

| JP | 55086463 | * | 6/1980 | ............. A61J/3/07 |
| JP | 61-76413 | * | 4/1986 | |
| JP | 09-216818 | | 8/1997 | |
| JP | 09216818 | * | 8/1997 | ............. A61K/9/48 |
| JP | 2001-170137 | | 6/2001 | |
| WO | WO 99/46329 | | 9/1999 | |
| WO | WO 9946329 | * | 9/1999 | ............ C08L/29/04 |

OTHER PUBLICATIONS

Translation to Fujio et al. (JP 55086463).*
Translation to Makoto et al. (JP 09216818).*
W. J. Bowtle, "Liquid Filling of Hard Gelatin Capsules: A New Technology for Alternative Formulations," Pharmaceutical Technology Europe, Oct., p. 84, 86 and 88–90, 1998.

* cited by examiner

Primary Examiner—Kelechi C. Egwim
(74) Attorney, Agent, or Firm—Knobbe, Martens Olson & Bear LLP

(57) ABSTRACT

A hard capsule which is made mainly of a polymer or copolymer obtained by polymerizing or copolymerizing at least one polymerizable vinyl monomer in the presence of polyvinyl alcohol and/or a derivative thereof. Unlike conventional hard capsules, this hard capsule can be filled with a solvent (e.g., polyethylene glycol) for a sparingly soluble drug ingredient.

9 Claims, 2 Drawing Sheets

FILLED CAPSULE

HARD CAPSULE

This application is the U.S. National Phase under 35 U.S.C. §371 of International Application PCT/JP01/07244, filed Aug. 24, 2001, which claims priority to Japanese Patent Application No. 2000-259830, filed Aug. 29, 2000. The International Application was not published under PCT Article 21(2) in English.

TECHNICAL FIELD

The present invention relates to a hard capsule that is made mainly of a polymer or copolymer obtained by polymerizing or copolymerizing at least one polymerizable vinyl monomer in the presence of polyvinylalcohol and/or a derivative thereof.

BACKGROUND ART

Many active substances (i.e. therapeutic ingredients) of medicines have poor solubility in water; with such substances, the absorbability from the alimentary canal is low, and hence the utilizability, the expression of therapeutic effects and so on are prone to dropping or fluctuating. In preclinical trials, when searching for therapeutic effects or biopharmaceutical parameters in animals or the like, it is common to make the therapeutic ingredient more easily absorbable by dissolving it in some kind of solvent; for a sparingly soluble therapeutic ingredient, polyethylene glycol of relatively low molecular weight or a derivative thereof, a polyoxyethylene sorbitan fatty acid ester, a fatty acid having 6 to 12 carbon atoms or a salt thereof, polyoxyethylene castor oil, a derivative of diethylene glycol, or the like is used. However, these solvents are generally liquids, and hence making tablets is difficult, and moreover the pharmaceutical form ultimately put onto the market is developed separately. If these solvents could be made into a pharmaceutical preparation directly, then the time required for making the pharmaceutical preparation could be greatly reduced; the most promising pharmaceutical form for this is a capsule. However, there is a drawback in that if a conventional gelatin hard capsule is filled with polyethylene glycol having a degree of polymerization of 400 (PEG 400), then moisture in the capsule skin migrates into the solvent, and the capsule may split (Pharmaceutical Technology Europe, Oct., 84, 86, 88–90, 1998). Moreover, with a conventional cellulose derivative capsule, the above solvents act as plasticizers, and hence a so-called 'sweating' phenomenon occurs on the surface of the capsule in which the solvent permeates through the capsule skin.

DISCLOSURE OF THE INVENTION

The present inventors carried out assiduous studies to attain the above object, and as a result discovered that a hard capsule that is made mainly of a polymer or copolymer obtained by polymerizing or copolymerizing at least one polymerizable vinyl monomer in the presence of polyvinylalcohol and/or a derivative thereof has excellent stability even when filled with a solvent for dissolving a sparingly soluble therapeutic ingredient, and moreover is also excellent in terms of general properties that a hard capsule should possess such as water solubility.

That is, in the present invention it was discovered that a hard capsule can be manufactured whereby, by using PVA as a base polymer, the strength of the capsule is maintained even when filled with PEG 400 or the like, and moreover by using a polymer or the like of acrylic acid or methacrylic acid and a derivative thereof, the capsule does not tend to soften even under conditions of high humidity within a practical range, and tends not to split even at low humidity.

The present invention provides the following hard capsules.

Item 1. A hard capsule, that is made mainly of a polymer or copolymer obtained by polymerizing or copolymerizing at least one polymerizable vinyl monomer in the presence of polyvinylalcohol and/or a derivative thereof.

Item 2. A hard capsule, that is made mainly of a polymer or copolymer obtained by polymerizing or copolymerizing at least one polymerizable vinyl monomer in the presence of polyvinylalcohol.

Item 3. The hard capsule described in item 1, wherein the polyvinylalcohol derivative is polyvinylalcohol having a thiol group at an end thereof.

Item 4. The hard capsule described in item 1 or 2, wherein the polymerizable vinyl monomer(s) is/are at least one selected from the group consisting of:

(1) acrylic acid, methacrylic acid, fumaric acid, maleic acid, and itaconic acid;

(2) sodium salts, potassium salts, ammonium salts and alkylamine salts of the compounds in (1); and (3) methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, acrylonitrile, acrylamide, dimethylacrylamide, styrene, vinyl acetate, hydroxyethyl methacrylate, hydroxyethyl acrylate, an ester formed by polyethylene glycol and methacrylic acid, an ester formed by polyethylene glycol and acrylic acid, an ester formed by polypropylene glycol and methacrylic acid, an ester formed by polypropylene glycol and acrylic acid, N-vinylpyrrolidone, and acryloyl morpholine.

Item 5. The hard capsule described in item 1 or 2, wherein the polymerizable vinyl monomer is a compound represented by general formula [1]

$$H_2C=C(R_1)-COOR_2 \quad [1]$$

[in the formula, $R_1$ represents a hydrogen atom or a methyl group, and $R_2$ represents a hydrogen atom or an alkyl group having 1 to 4 carbon atoms].

Item 6. The hard capsule described in item 1 or 2, wherein the polymerizable vinyl monomers are acrylic acid or methacrylic acid and methyl methacrylate, and the acrylic acid or methacrylic acid is 5 to 10 wt % of the total amount of the polymerizable vinyl monomers, and the methyl methacrylate is 50 to 95 wt % of the total amount of the polymerizable vinyl monomers.

Item 7. The hard capsule described in item 1 or 2, wherein the polyvinylalcohol and/or derivative thereof is 20 to 95 wt %, and the polymerizable vinyl monomer(s) is/are 5 to 80 wt %.

Item 8. The hard capsule described in any one of items 1 to 7, further containing a gelating agent.

Item 9. The hard capsule described in any one of items 1 to 8, wherein the inside of the capsule is filled with polyethylene glycol having a degree of polymerization of 2000 or less or a derivative thereof.

Item 10. The hard capsule described in any one of items 1 to 8, wherein the inside of the capsule is filled with a polyoxyethylene sorbitan fatty acid ester.

Item 11. The hard capsule described in any one of items 1 to 8, wherein the inside of the capsule is filled with a fatty acid having 6 to 12 carbon atoms or a salt thereof.

Item 12. The hard capsule described in any one of items 1 to 8, wherein the inside of the capsule is filled with polyoxyethylene castor oil.

Item 13. The hard capsule described in anyone of items 1 to 8, wherein the inside of the capsule is filled with an ether derivative of diethylene glycol.

Item 14. The hard capsule described in any one of items 9 to 13, wherein a thickener is further added to the inside of the capsule.

Following is a more detailed description of the present invention.

Regarding the polyvinylalcohol and derivative thereof used in the present invention, in addition to a completely hydrolyzed substance, an intermediately hydrolyzed substance or a partially hydrolyzed substance, various modified PVAs such as amine-modified PVA, ethylene-modified PVA and terminal-thiol-modified PVA can be used.

PVA is a macromolecular compound, and ones of various degrees of polymerization are known, but there are no particular limitations on the mean degree of polymerization, with it being preferable to select one that is optimum in terms of concentration and viscosity in accordance with the usage. That is, there are various methods of manufacturing the hard capsule as shown in the item below, and the optimum viscosity varies according to the method, and hence the molecular weight of PVA usable can be selected as appropriate.

Polymerizable vinyl monomers that can be used in the present invention include, for example:
at least one selected from the group consisting of:
(1) acrylic acid, methacrylic acid, fumaric acid, maleic acid, and itaconic acid;
(2) sodium salts, potassium salts, ammonium salts and alkylamine salts of the compounds in (1); and
(3) methyl methacrylate, methyl acrylate, ethyl methacrylate, ethyl acrylate, butyl methacrylate, butyl acrylate, isobutyl methacrylate, isobutyl acrylate, cyclohexylmethacrylate, cyclohexylacrylate, 2-ethylhexyl methacrylate, 2-ethylhexyl acrylate, acrylonitrile, acrylamide, dimethylacrylamide, styrene, vinyl acetate, hydroxyethyl methacrylate, hydroxyethyl acrylate, an ester formed by polyethylene glycol and methacrylic acid, an ester formed by polyethylene glycol and acrylic acid, an ester formed by polypropylene glycol and methacrylic acid, an ester formed by polypropylene glycol and acrylic acid, N-vinylpyrrolidone, and acryloyl morpholine; and compounds represented by general formula [1]

$$H_2C=C(R_1)-COOR_2 \quad [1]$$

[in the formula, $R_1$ represents a hydrogen atom or a methyl group, and $R_2$ represents a hydrogen atom or an alkyl group having 1 to 4 carbon atoms].

Preferably, at least one from (1) and (2) and at least one from (3) are used. More preferably, acrylic acid or methacrylic acid and methyl methacrylate are used.

There are no particular limitations on the amounts used of the PVA and/or derivative thereof and the polymerizable vinyl monomer(s), but preferably the amount used of the PVA and/or derivative thereof is from 20 to 95 wt %, and the amount used of the polymerizable vinyl monomer(s) from 5 to 80 wt %. More preferably, the amount used of the PVA and/or derivative thereof is from 50 to 90 wt %, and the amount used of the polymerizable vinyl monomer(s) from 10 to 50 wt %.

If the amount used of the PVA and/or derivative thereof is less than 20 wt %, then there will be a risk of the ability of the capsule to dissolve or be dispersed in water being somewhat reduced compared with the case that 20 wt % or more is used. On the other hand, if the amount used exceeds 95 wt %, then there will be a risk of the capsule being affected by humidity somewhat more, and hence the strength dropping somewhat and softening occurring under high humidity, compared with the case that 95 wt % or less is used.

Moreover, in the case that at least one from (1) and (2) and at least one from (3) are used as polymerizable vinyl monomers, relative to the total amount of the polymerizable vinyl monomers, the amount used of the at least one from (1) and (2) is from 5 to 50 wt %, preferably from 10 to 40 wt %, and the amount used of the at least one from (3) is from 50 to 95 wt %, preferably from 60 to 90 wt %.

A publicly known method can be used as the method of polymerization or copolymerization; for example, the PVA and/or derivative thereof is added to water and is dissolved by heating, and next the at least one polymerizable vinyl monomer and a polymerization initiator are added, and polymerization or copolymerization is made to occur, whereupon a resin can be obtained.

The polymerization initiator is used as required, and one used conventionally can be used. For example, an azo compound such as 2,2-azobis(2-amidinopropane) hydrochloride or AIBN (azoisobutyronitrile), a persulfate such as potassium persulfate, sodium persulfate or ammonium persulfate, an organic peroxide such as t-butyl hydroperoxide, a redox initiator such as hydrogen peroxide—tartaric acid or hydrogen peroxide—sodium tartrate, and so on, can be used.

Methods of manufacturing the hard capsule of the present invention include an injection molding method and a dipping method, but there is no particular limitation to these methods, so long as the method is such that the hard capsule can be molded. The dipping method is a capsule manufacturing method that makes use of gelation of the hard capsule base material due to a temperature difference; in the case that the base material cannot be gelated, a so-called gelating agent is added. For example, there are proposals in Japanese Patent No. 2552937 regarding a gelating agent used when manufacturing a hard capsule having a water-soluble cellulose derivative as a base material. The gelating agent is selected as appropriate in accordance with the compatibility with the capsule base material, but specific examples are kappa carrageenan, iota carrageenan, lambda carrageenan, tamarind seed polysaccharide, pectin, curdlan, gelatin, furcellaran, agar, xanthan gum, locust bean gum, jielan gum, and so on.

Moreover, a gelation auxiliary can be used as required. As a gelation auxiliary, for kappa carrageenan, a water-soluble compound containing one or two or more of potassium ions, ammonium ions and calcium ions, for example potassium chloride, potassium phosphate, calcium chloride or ammonium chloride, can be used, and for iota carrageenan, a water-soluble compound containing calcium ions, for example calcium chloride, can be used.

An example will now be given of a method of manufacturing the hard capsule in the case that a gelating agent is used. The hard capsule can be obtained by a method similar to a normal hard gelatin capsule molding procedure, namely a molding pin is immersed in an aqueous solution (gel) in which have been dissolved the polymer or copolymer obtained by polymerizing or copolymerizing at least one polymerizable vinyl monomer in the presence of polyvinylalcohol and/or a derivative thereof, the gelating agent, and if necessary a gelation auxiliary, and then the molding pin is pulled out, and the above-mentioned polymer or copolymer is gelated and dried.

Note that, as with a normal hard gelatin capsule or cellulose derivative capsule, colorants such as dyes and pigments, opacifying agents, fragrances and so on can if required be added to the hard capsule of the present invention as appropriate from within ranges such that the effects of the present invention are not impeded.

The amounts used of the gelating agent, the gelation auxiliary and other additives are selected as appropriate from within ranges such that the hard capsule can be manufactured.

There are no particular limitations on the thickness of the hard capsule of the present invention, provided that the functions of the hard capsule are fulfilled; the thickness is preferably about 0.01 to 5 mm, more preferably 0.05 to 1 mm.

A characteristic feature of the hard capsule of the present invention is that it can be filled even with a solvent such as PEG 400 that is used for dissolving a sparingly soluble therapeutic ingredient but causes splitting or the like due to migration of moisture with a conventional hard capsule, or something such as creosote where the therapeutic ingredient exerts an adverse effect on the stability of the hard capsule. There are no particular limitations on the solvent filled, provided the functions of the capsule are not impaired; examples include low molecular weight polyethylene glycol (PEG) and fatty acid ester derivatives thereof, ether derivatives of diethylene glycol, polyhydric alcohol fatty acid esters, propylene glycol fatty acid esters, glycerol fatty acid esters, polyglycerol fatty acid esters, polyoxyethylene glycerol fatty acid esters, sorbitan fatty acid esters, polyoxyethylene sorbitan fatty acid esters, polyoxyethylene sorbit fatty acid esters, polyoxyethylene castor oil, medium-chain fatty acids and salts thereof, and substances including the above. With the hard capsule of the present invention, in addition to the above, there are no limitations whatsoever on filling with other additives commonly used in hard capsules such as lactose and starches.

Pharmaceutical contrivances such as making the filling operation easier or preventing leakage of the filling from out of the hard capsule can be achieved by adding a thickener for the above-mentioned solvent. There are no particular limitations on the thickener, so long as it is one mentioned in pharmaceutics textbooks or the like or one that is commonly used, for example light silicic acid anhydride, a vegetable oil, or a cellulose derivative.

There are no particular limitations on the therapeutic ingredient filled into the hard capsule of the present invention, provided it does not impair the functioning of the capsule. As medicines, examples include vitamins, antifebriles, analgesics, antiphlogistics, anti-ulcer agents, cardiotonics, anticoagulants, anastaltics, bone resorption inhibitors, vascularization inhibitors, antidepressants, antitumor agents, antitussives/expectorants, muscle relactants, antiepileptics, anti-allergic agents, arrhythmia treating agents, vasodilators, depressors/diuretics, diabetes treating agents, anti-tuberculosis agents, hormones, antinarcotics, antibacterials, antifungals, antivirals, and so on; however, there is no particular limitation to these pharmacological action groups, but rather everything containing a therapeutic ingredient that has relatively poor solubility in water may be a target for the hard capsule of the present invention. Preferably, the therapeutic ingredient is a sparingly soluble active substance.

In addition to a pharmaceutical preparation for oral administration, the hard capsule of the present invention can also be used as an inhalant or as a pharmaceutical preparation for rectal administration. Moreover, in addition to drugs for medical treatment, the hard capsule of the present invention can also be used in the fields of drugs/chemicals for animals or plants, cosmetics, and foodstuffs. Furthermore, the hard capsule of the present invention can also be filled with reagents or the like for assaying or synthesis, and used with an object of simplifying handling thereof.

BEST MODE FOR CARRYING OUT THE INVENTION

Figure 1:
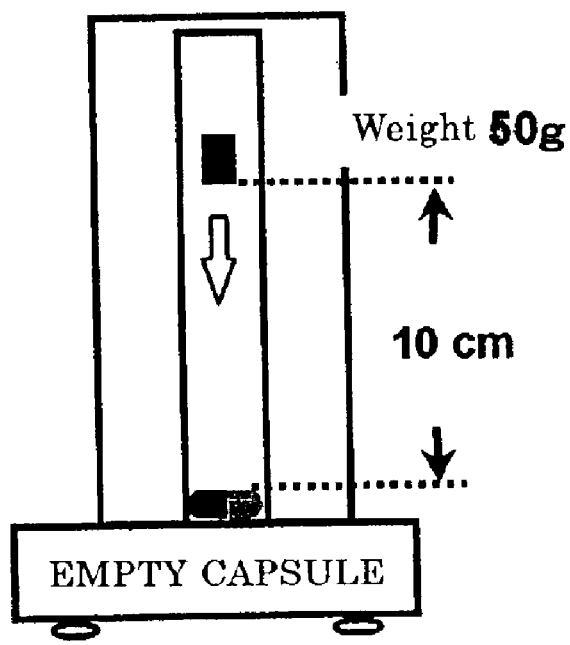
FIG. 1 is a schematic drawing showing a hard capsule hardness test apparatus.

Following is a detailed description of the present invention, with working examples divided into synthesis examples, a manufacturing example, evaluation tests and experimental examples being shown; however, the present invention is not limited to the following working examples. Moreover, '%' indicates wt % in all cases.

SYNTHESIS EXAMPLE 1

75 parts by weight of PVA-SH (degree of polymerization 500, degree of hydrolysis 88%, made by Kuraray Co., Ltd.) was completely dissolved in 237 parts by weight of ion-exchange water at 95° C. Next, the amounts of methacrylic acid and methyl methacrylate shown in Table 1 below were added, and after purging with nitrogen gas 3 parts by weight of t-butyl hydroperoxide was added and reaction was carried out, thus producing compounds E-1001, E-1002, E-1003 and E-1004. An aqueous solution of 15 to 20% of each of the components was prepared, and approximately 0.1 mm films were produced using a casting method. The solubilities (water solubility, solubility at pH 1.2, solubility at pH 6.8, solubility in PEG 400) and strengths (bending angle (RH 65%, dry state)) of the films produced are shown in Table 1.

In the water solubility tests, a piece of film of size 20 mm square was immersed in 10 ml of water, gentle shaking was carried out, and it was ascertained whether or not the film dissolved or dispersed. In the pH 1.2 solubility tests, a piece of film of size 20 mm square was immersed in 10 ml of Japanese Pharmacopoeia first fluid (pH 1.2) prepared from hydrochloric acid and deionized water, gentle shaking was carried out, and it was ascertained whether or not the film dissolved or dispersed. In the pH 6.8 solubility tests, a piece of film of size 20 mm square was immersed in 10 ml of Japanese Pharmacopoeia second fluid (pH 6.8) prepared from potassium dihydrogenphosphate, sodium hydroxide and deionized water, gentle shaking was carried out, and it was ascertained whether or not the film dissolved or dispersed. In the PEG 400 solubility tests, a piece of film of size 20 mm square was immersed in 10 ml of polyethylene glycol (molecular weight 400) and was left at 60° C. for one week, and then it was ascertained whether or not the film dissolved.

Moreover, in the strength tests, a piece of film of size 10 mm×20 mm (thickness 0.1 mm) was aged for at least 24 hours at a relative humidity of 65% or in a dry state, and then the film was bent slowly 45° at a time, and the angle at which the film snapped was measured in units of 45°.

TABLE 1

Polymer composition ratios and film property values for Synthesis Example 1

|  | E-1001 | E-1002 | E-1003 | E-1004 |
|---|---|---|---|---|
| Composition |  |  |  |  |
| PVA-SH | 75 | 80 | 80 | 80 |
| MAA | 5 | 6 | 4 | 2 |
| MMA | 20 | 14 | 16 | 180 |
| Film solubility |  |  |  |  |
| Water solubility | Yes | Yes | Yes | Yes |
| pH1.2 solubility | Yes | Yes | Yes | Yes |
| pH6.8 solubility | Yes | Yes | Yes | Yes |
| PEG400 | No | No | No | No |
| Film strength |  |  |  |  |
| Bending angle[1] | 180° | 180° | 180° | 180° |
| Bending angle[2] | 90° | 135° | 135° | 135° |

Bending angle[1]: Stored at relative humidity of 65%
Bending angle[2]: Stored in dry state
PVA-SH: polyvinylalcohol having terminal thiol group,
MAA: methacrylic acid,
MMA: methyl methacrylate
Yes: Soluble
No: Insoluble

SYNTHESIS EXAMPLE 2

75 parts by weight of PVA-SH (degree of polymerization 500 and 1500 mixed together, both degree of hydrolysis 88%, made by Kuraray Co., Ltd.) was completely dissolved in 237 parts by weight of ion-exchange water at 95° C. Next, the amounts of acrylic acid and methyl methacrylate shown in Table 2 below were added, and after nitrogen substitution 3 parts by weight of t-butyl hydroperoxide was added and reaction was carried out, thus producing compounds E-2001, E-2002, E-2003, E-2004, E-2005 and E-2006. The mixing proportions of the PVA-SH of degree of polymerization 500 and the PVA-SH of degree of polymerization 1500 were 50:50 (E-2001), 50:50 (E-2002), 45:55 (E-2003), 40:60 (E-2004), 20:80 (E-2005) and 10:90 (E-2006). An aqueous solution of 15 to 20% of each of the components was prepared, and approximately 0.1 mm films were produced using a casting method. The solubilities and strengths of the films produced were measured as in Synthesis Example 1, and are shown in Table 2.

TABLE 2

Polymer composition ratios and film property values for Synthesis Example 2

|  | E-2001 | E-2002 | E-2003 | E-2004 | E-2005 | E-2006 |
|---|---|---|---|---|---|---|
| Composition |  |  |  |  |  |  |
| PVA-SH | 75 | 75 | 75 | 75 | 75 | 75 |
| AA | 7.5 | 5 | 7.5 | 7.5 | 7.5 | 7.5 |
| MMA | 17.5 | 20 | 17.5 | 17.5 | 17.5 | 17.5 |
| Film solubility |  |  |  |  |  |  |
| Water solubility | Yes | Yes | Yes | Yes | Yes | Yes |
| pH1.2 solubility | Yes | Yes | Yes | Yes | Yes | Yes |
| pH6.8 solubility | Yes | Yes | Yes | Yes | Yes | Yes |
| PEG400 | No | No | No | No | No | No |
| Film strength |  |  |  |  |  |  |
| Bending angle[1] | 180° | 180° | 180° | 180° | 180° | 180° |
| Bending angle[2] | 180° | 180° | 180° | 180° | 180° | 180° |

Bending angle[1]: Stored at relative humidity of 65%
Bending angle[2]: Stored in dry state
PVA-SH: polyvinylalcohol having terminal thiol group,
AA: acrylic acid,
MMA: methyl methacrylate
Yes: Soluble
No: Insoluble

SYNTHESIS EXAMPLE 3

75 parts by weight of PVA-SH (degree of polymerization 500 and 1500 mixed together in a ratio of 1:9, both degree of hydrolysis 88%, made by Kuraray Co., Ltd.) was completely dissolved in 237 parts by weight of ion-exchange water at 95° C. The amounts of methacrylic acid and methyl methacrylate shown in Table 3 below were then added thereto, and after nitrogen substitution 3 parts by weight of t-butyl hydroperoxide was added and reaction was carried out, thus producing compounds E-3001, E-3002, E-3003. An aqueous solution of 15 to 20% of each of the components was prepared, and approximately 0.1 mm films were produced using a casting method. The solubilities and strengths of the films produced were measured as in Synthesis Example 1, and are shown in Table 3.

TABLE 3

Polymer composition ratios and film property values for Synthesis Example 3

|  | E-3001 | E-3002 | E-3003 |
|---|---|---|---|
| Composition |  |  |  |
| PVA-SH | 75 | 75 | 75 |
| MAA | 7.5 | 10 | 5 |
| MMA | 17.5 | 15 | 20 |
| Film solubility |  |  |  |
| Water solubility | Yes | Yes | Yes |
| pH1.2 solubility | Yes | Yes | Yes |
| pH6.8 solubility | Yes | Yes | Yes |
| PEG400 | No | No | No |
| Film strength |  |  |  |
| Bending angle[1] | 180° | 180° | 180° |
| Bending angle[2] | 90° | 90° | 90° |

Bending angle[1]: Stored at relative humidity of 65%
Bending angle[2]: Stored in dry state
PVA-SH: polyvinylalcohol having terminal thiol group,
MAA: methacrylic acid,
MMA: methyl methacrylate
Yes: Soluble
No: Insoluble

SYNTHESIS EXAMPLE 4

75 parts by weight of PVA (degree of polymerization 500 and 1700, both degree of hydrolysis 88%, made by Nippon Synthetic Chemical Industry Co., Ltd.) was completely dissolved in 237 parts by weight of ion-exchange water. Next, the amounts of acrylic acid and methyl methacrylate shown in Table 4 below were added, and after nitrogen substitution 3 parts by weight of t-butyl hydroperoxide was added and reaction was carried out, thus producing compounds E-4001, E-4002, E-4003, E-4004, E-4005 and E-4006. The mixing proportions of the PVA of degree of polymerization 500 and the PVA of degree of polymerization 1700 were 50:50 (E-4001), 50:50 (E-4002), 45:55 (E-4003), 40:60 (E-4004), 20:80 (E-4005) and 10:90 (E-4006). An aqueous solution of 15 to 20% of each of the components was prepared, and approximately 0.1 mm films were produced using a casting method. The solubilities and strengths of the films produced were measured as in Synthesis Example 1, and are shown in Table 4.

TABLE 4

|  | E-4001 | E-4002 | E-4003 | E-4004 | E-4005 | E-4006 |
|---|---|---|---|---|---|---|
| Composition |  |  |  |  |  |  |
| PVA | 75 | 75 | 75 | 75 | 75 | 75 |
| AA | 7.5 | 5 | 7.5 | 7.5 | 7.5 | 7.5 |
| MMA | 17.5 | 20 | 17.5 | 17.5 | 17.5 | 17.5 |
| Film solubility |  |  |  |  |  |  |
| Water solubility | Yes | Yes | Yes | Yes | Yes | Yes |
| pH1.2 solubility | Yes | Yes | Yes | Yes | Yes | Yes |
| pH6.8 solubility | Yes | Yes | Yes | Yes | Yes | Yes |
| PEG400 solubility | No | No | No | No | No | No |
| Film strength |  |  |  |  |  |  |
| Bending angle[1] | 180° | 180° | 180° | 180° | 180° | 180° |
| Bending angle[2] | 180° | 180° | 180° | 180° | 180° | 180° |

Bending angle[1]: Stored at relative humidity of 65%
Bending angle[2]: Stored in dry state
PVA: polyvinylalcohol,
AA: acrylic acid,
MMA: methyl methacrylate
Yes: Soluble
No: Insoluble Evaluation Test 1: Hard Capsule Softening Degree Test An empty hard capsule was placed on its side, a plunger of diameter 3.5 mm was pushed against the capsule at a constant speed of 5 mm/min, and the maximum strength until the diameter of the capsule was halved was measured.

Evaluation Test 2: Hard Capsule Appearance Test

Hard capsules filled with various additives were stored for 5 days sealed tightly at 60° C. or for 7 days at room temperature, and then the shapes of the capsules were verified with the naked eye.

Evaluation Test 3: Hard Capsule Dissolution Test

An empty hard capsule was separated into the cap and the body part, 50 ml of water at 37±2° C. was added to the one hard capsule, agitation was carried out occasionally, and the time taken for the hard capsule to completely dissolve was measured.

Evaluation Test 4: Hard Capsule Disintegration Test

The hard capsule disintegration time was measured in accordance with the disintegration test method in the Japanese Pharmacopoeia 13th edition. For about 1000 ml of water, and Japanese Pharmacopoeia first fluid (pH 1.2) and second fluid (pH 6.8), a capsule with the cap and body part joined together was set in a disintegration testing machine following the normal method and a disc was placed on top, and the time required for disintegration was measured.

Evaluation Test 5: Hard Capsule Hardness Test

Using the hard capsule hardness test apparatus shown in FIG. 1, the strength of an empty hard capsule was measured. That is, the damage to the hard capsule when a weight of 50 grams was dropped vertically onto the empty capsule from 10 cm was investigated.

Evaluation Test 6: Hard Capsule Pressure Resistant Test

Figure 2:
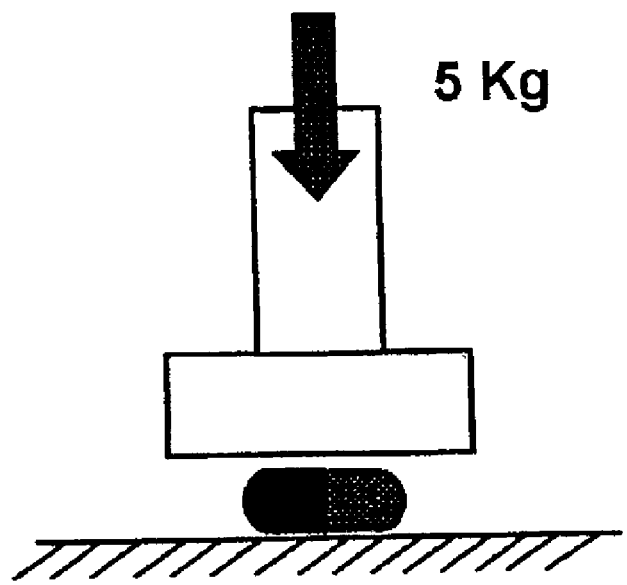
FIG. 2 is a schematic drawing showing a hard capsule pressure resistant strength test apparatus.

Using the hard capsule pressure resistant test apparatus shown in FIG. 2, the resistant of a hard capsule was measured. That is, the damage to the hard capsule when the hard capsule was pressed with a force of 5 kilograms was investigated.

EXPERIMENTAL EXAMPLE 1

Hard capsules (with no filling) produced by the method in the Manufacturing Example using polymers of Synthetic Examples 1, 2, 3 and 4 as raw materials were stored for 1 day at 25° C. and RH 75%, and then the strength of each of the capsules was measured using the method of Evaluation Test 1. The measurement results are shown in Table 5.

TABLE 5

| | Hard capsule softening degree test | | | | | | | | | | | | | | | | |
|---|---|---|---|---|---|---|---|---|---|---|---|---|---|---|---|---|---|
| Hard capsule | E-1001 | E-1002 | E-1003 | E-1004 | E-2001 | E-2002 | E-2003 | E-2004 | E-2005 | E-2006 | E-3001 | E-4001 | E-4002 | E-4003 | E-4004 | E-4005 | E-4006 |
| Strength (grams) | 97 | 128 | 148 | 160 | 170 | 212 | 224 | 162 | 170 | 180 | 136 | 180 | 200 | 212 | 194 | 180 | 165 |

MAMUFACTURING EXAMPLE 0.40 grams of carrageenan and 0.30 grams of potassium chloride were added to 200 grams of aqueous solutions of the polymers produced in Synthesis Examples 1, 2, 3 and 4 prepared such that the nonvolatile content was about 20 to 23%, this was kept at about 60° C., and a stainless steel pin at room temperature was put in and then pulled out, thus manufacturing hard capsules of film thickness about 0.1 to 0.2 mm.

EXPERIMENTAL EXAMPLE 2

The solubilities of hard capsules produced by the method in the Manufacturing Example using the polymers of Synthetic Examples 1, 2 and 4 as raw materials, and a commercially available gelatin capsule (marketing name: Gelatin Capsule; made by Shionogi Qualicaps Co., Ltd.) and hydroxypropylmethylcellulose capsule (marketing name: Cellcap; made by Shionogi Qualicaps Co., Ltd.) (hereinafter referred to as the HPMC capsule), were measured using the method of Evaluation Test 3. The measurement results are shown in Table 6.

TABLE 6

Hard capsule dissolution time (minutes; water, 37° C.)

| Hard capsule | Gelatin | HPMC | E-1001 | E-1002 | E-1003 | E-1004 | E-2001 | E-2002 | E-2003 | E-2004 | E-2005 | E-2006 | E-4001 | E-4002 | E-4003 | E-4004 | E-4005 | E-4006 |
|---|---|---|---|---|---|---|---|---|---|---|---|---|---|---|---|---|---|---|
| Dissolution time (min) | 3.5 | 8.2 | 6.3 | 6.8 | 4.5 | 5.3 | 7.7 | 9.8 | 11.3 | 11.0 | 9.5 | 8.7 | 6.8 | 8.8 | 9.2 | 9.6 | 8.8 | 7.4 |

EXPERIMENTAL EXAMPLE 3

Five of each of the hard capsules produced by the method in the Manufacturing Example using polymers of Synthetic Examples 1, 2, 3 and 4 as raw materials, and the commercially available Gelatin Capsule and HPMC capsule, were prepared, storage was carried out for 3 days under conditions of room temperature and a relative humidity of 57%, and the strengths were measured using the method of Evaluation Test 5. The measurement results are shown in Table 7.

TABLE 7

Strength upon storage of hard capsules

| Capsule | Moisture value (%) | Splitting |
|---|---|---|
| Gelatin | 14.2 | 0/5 |
| HPMC | 6.4 | 0/5 |
| E-1001 | 6.8 | 0/5 |
| E-1002 | 7.2 | 0/5 |
| E-1003 | 6.9 | 0/5 |
| E-1004 | 6.7 | 0/5 |
| E-2001 | 7.1 | 0/5 |
| E-2002 | 6.7 | 0/5 |
| E-2003 | 6.7 | 0/5 |
| E-2004 | 6.7 | 0/5 |
| E-2005 | 6.9 | 0/5 |
| E-2006 | 6.8 | 0/5 |
| E-3001 | 6.7 | 0/5 |
| E-4001 | 6.6 | 0/5 |
| E-4002 | 6.8 | 0/5 |
| E-4003 | 6.3 | 0/5 |
| E-4004 | 7.1 | 0/5 |
| E-4005 | 6.5 | 0/5 |
| E-4006 | 6.5 | 0/5 |

EXPERIMENTAL EXAMPLE 4

0.5 ml of PEG 400 or a polyoxyethylene sorbitan fatty acid ester (marketing name: Tween 80) was filled into hard capsules produced by the method in the Manufacturing Example using polymers of Synthetic Examples 2, 3 and 4 as raw materials, and the commercially available gelatin capsule and HPMC capsule, storage was carried out for 5 days sealed tightly at 60° C., and then the appearance and the pressure resistant were measured using the methods of Evaluation Tests 2 and 6. The measurement results are shown in Table 8.

TABLE 8

Appearance and pressure resistant of hard capsules filled with solvents during stress tests

| Capsule | PEG400 Appearance | PEG400 Splitting | Tween80 Appearance | Tween80 Splitting |
|---|---|---|---|---|
| Gelatin | No change | 2/2 | Deformed slightly | 0/2 |
| HPMC | Deformed | 0/2 | Deformed slightly | 0/2 |
| E-2001 | No change | 0/2 | No change | 0/2 |
| E-2002 | No change | 0/2 | No change | 0/2 |
| E-2003 | No change | 0/2 | No change | 0/2 |
| E-2004 | No change | 0/2 | No change | 0/2 |
| E-2006 | No change | 0/2 | No change | 0/2 |
| E-3001 | No change | 0/2 | No change | 0/2 |
| E-4001 | No change | 0/2 | No change | 0/2 |
| E-4002 | No change | 0/2 | No change | 0/2 |
| E-4003 | No change | 0/2 | No change | 0/2 |
| E-4004 | No change | 0/2 | No change | 0/2 |
| E-4005 | No change | 0/2 | No change | 0/2 |
| E-4006 | No change | 0/2 | No change | 0/2 |

EXPERIMENTAL EXAMPLE 5

0.5 ml of PEG 400, or a glyceryl fatty acid ester of PEG (marketing name: Labrasol), or a polyoxyethylene sorbitan fatty acid ester (marketing name: Tween 80) was filled into hard capsules produced by the method in the Manufacturing Example using polymers of Synthetic Examples 2 (E-2006) and 4 (E-4006) as raw materials, and the disintegration time was measured using the method of Evaluation Test 4. The measurement results are shown in Table 9.

TABLE 9

Disintegration time of hard capsules (minutes; water, 37° C.)

| Filling | E-2006 Water | E-2006 First fluid | E-2006 Second fluid | E-4006 Water | E-4006 First fluid | E-4006 Second fluid |
|---|---|---|---|---|---|---|
| PEG400 | 4.6 | 5.8 | 5.2 | 4.2 | 6.2 | 6.0 |
| Labrasol | 5.1 | 4.3 | 4.5 | 5.8 | 5.0 | 4.0 |
| Tween80 | 6.5 | 12.2 | 14.3 | 5.2 | 10.2 | 8.6 |

EXPERIMENTAL EXAMPLE 6

0.5 ml of PEG 400, a glyceryl fatty acid ester of PEG (marketing name: Labrasol), a polyoxyethylene sorbitan fatty acid ester (marketing name: Tween 80), capric acid, a diethylene glycol derivative (marketing name: Transcutol P), or propylene glycol was filled into hard capsules produced by the method in the Manufacturing Example using polymers of Synthetic Examples 2 (E-2006) and 4 (E-4006) as raw materials, and the commercially available gelatin capsule and HPMC capsule, storage was carried out for 1 week at room temperature, and then the appearance and the compression strength of the hard capsules were measured using the methods of Evaluation Tests 2 and 6. The measurement results are shown in Table 10.

TABLE 10

Appearance and compression strength upon storing at room temperature (1 week) when filled with a solvent

| Filling | E-2006 Appearance | Splitting | E-4006 Appearance | Splitting | HPMC Appearance | Splitting | Gelatin Appearance | Splitting |
|---|---|---|---|---|---|---|---|---|
| PEG400 | No change | 0/2 | No change | 0/2 | Deformed slightly | 0/2 | No change | 2/2 |
| Labrasol | No change | 0/2 | No change | 0/2 | Deformed slightly | 0/2 | Deformed slightly | 0/2 |
| Tween80 | No change | 0/2 | No change | 0/2 | Deformed slightly | 0/2 | No change | 1/2 |
| Capric acid | No change | 0/2 | No change | 0/2 | Deformed slightly | 0/2 | No change | 1/2 |
| Transcutol P | No change | 0/2 | No change | 0/2 | Deformed | 2/2 | No change | 2/2 |
| Propylene glycol | No change | 0/2 | No change | 0/2 | Deformed | 2/2 | Deformed | 2/2 |

EXPERIMENTAL EXAMPLE 7

40 parts by weight of white beeswax was added to 960 parts by weight of PEG 400, and mixing was carried out with stirring at 70° C. 0.5 ml of this was filled into hard capsules produced by the method in the Manufacturing Example using polymers of Synthetic Examples 2 (E-2006) and 4 (E-4006) as raw materials, and the commercially available gelatin capsule and HPMC capsule, storage was carried out for 1 week at room temperature, and then the appearance and the compression strength of the hard capsules were measured using the methods of Evaluation Tests 2 and 6. The measurement results are shown in Table 11.

EXPERIMENTAL EXAMPLE 8

26 parts by weight of light silicic acid anhydride was added to 974 parts by weight of PEG 400, and mixing was carried out with stirring at 8000 rpm. 0.5 ml of this was filled into hard capsules produced by the method in the Manufacturing Example using polymers of Synthetic Examples 2 (E-2006) and 4 (E-4006) as raw materials, and the commercially available gelatin capsule and HPMC capsule, storage was carried out for 1 week at room temperature, and then the appearance and the compression strength of the hard capsules were measured using the methods of Evaluation Tests 2 and 6. The measurement results are shown-in Table 11.

Moreover, all of the films snap with difficulty when bent, and hence the polymers are suitable as hard capsule raw materials.

[Softening Degree of the Hard Capsule of the Present Invention]

As shown in Table 5, the hard capsule of the present invention has high strength even under high humidity, with softening not being observed.

[Solubility and Disintegration of the Hard Capsule of the Present Invention]

As shown in Table 6, the time for dissolution in water of the capsule of the present invention is within 12 minutes in all cases, i.e. the solubility is good. Moreover, as shown in Table 9, even when filled with PEG 400, Labrasol or Tween 80, the hard capsule of the present invention disintegrates rapidly in water and first fluid and second fluid.

[Impact Strength of the Hard Capsule of the Present Invention]

As shown in Table 7, the impact strength of the capsule of the present invention is comparable with that of a commercially available gelatin capsule and HPMC capsule, and hence it is judged that the capsule of the present invention can adequately be used as a hard capsule.

[Filling of Solvents into Hard Capsule of the Present Invention]

As shown in Table 8, when hard capsules filled with PEG 400 or Tween 80 are stored under severe conditions of 60°

TABLE 11

Appearance and compression strength upon storing at room temperature (1 week) when filled with a high viscosity filling

| Filling | E-2006 Appearance | Splitting | E-4006 Appearance | Splitting | HPMC Appearance | Splitting | Gelatin Appearance | Splitting |
|---|---|---|---|---|---|---|---|---|
| PEG400/ white beeswax | No change | 0/2 | No change | 0/2 | Deformed | 0/2 | No change | 2/2 |
| PEG400/ light silicic acid anhydride | No change | 0/2 | No change | 0/2 | Deformed | 0/2 | No change | 2/2 |

[Evaluation as Hard Capsule Raw Materials]

As shown in Tables 1, 2, 3 and 4, all of the polymers from E-1001 to E-4006 dissolve in water and acidic and neutral aqueous solutions, but do not dissolve in PEG 400.

C., the commercially available gelatin capsule and HPMC capsule show deformation and splitting, whereas the capsule of the present invention does not show deformation or splitting. Furthermore, as shown in Tables 10 and 11, the hard capsule of the present invention does not deform, and splitting is not observed, even when filled with any of various fillings.

INDUSTRIAL APPLICABILITY

According to the hard capsule of the present invention, pharmaceutical preparation becomes possible of a hard capsule filled with polyethylene glycol (PEG) of relatively low molecular weight or a derivative thereof, a polyoxyethylene sorbitan fatty acid ester, a fatty acid having 6 to 12 carbon atoms or a salt thereof, polyoxyethylene castor oil, a derivative of diethylene glycol, or the like, for which pharmaceutical preparation of a capsule is considered to be difficult with a conventional hard capsule from the standpoint of stability.

That is, the hard capsule of the present invention can be filled with many fillings that were considered to not be suitable with conventional hard capsules from the standpoint of change in appearance, strength and so on; the hard capsule of the present invention will thus contribute to improvement of the effective availability rate of drugs, simplification of pharmaceutical preparations, and rapid development of pharmaceutical preparations.

What is claimed is:

1. A hard capsule, that is made mainly of a polymer or copolymer obtained by polymerizing or copolymerizing at least one polymerizable vinyl monomer in the presence of polyvinylalcohol and/or a derivative thereof, wherein the polymerizable vinyl monomer is a compound represented by general formula $$H_2C=C(R_1)-COOR_2 \qquad [1].$$

2. A hard capsule, that is made mainly of a polymer or copolymer obtained by polymerizing or copolymerizing at least one polymerizable vinyl monomer in the presence of polyvinylalcohol and/or a derivative thereof, wherein the polymerizable vinyl monomers are acrylic acid or methacrylic acid and methyl methacrylate, and the acrylic acid or methacrylic acid is 5 to 50 wt % of the total amount of the polymerizable vinyl monomers, and the methyl methacrylate is 50 to 95 wt % of the total amount of the polymerizable vinyl monomers.

3. A hard capsule, that is made mainly of a polymer or copolymer obtained by polymerizing or copolymerizing at least one polymerizable vinyl monomer in the presence of polyvinylalcohol, wherein the polymerizable vinyl monomer is a compound represented by general formula $$H_2C=C(R_1)-COOR_2 \qquad [1].$$

4. The hard capsule according to claim 1 or 3, wherein the polyvinylalcohol and/or derivative thereof is 20 to 95 wt %, and the polymerizable vinyl monomer(s) is/are 5 to 80 wt %.

5. The hard capsule according to claim 1 or 3, further containing a gelating agent.

6. The hard capsule according to claim 1, wherein the inside of the capsule is filled with polyethylene glycol having a degree of polymerization of 2000 or less or a derivative thereof.

7. The hard capsule according to claim 1, wherein the inside of the capsule is filled with an ether derivative of diethylene glycol.

8. The hard capsule according to claim 6, wherein a thickener is further added to the inside of the capsule.

9. A hard capsule, that is made mainly of a polymer or copolymer obtained by polymerizing or copolymerizing at least one polymerizable vinyl monomer in the presence of polyvinylalcohol, wherein the polymerizable vinyl monomers are acrylic acid or methacrylic acid and methyl methacrylate, and the acrylic acid or methacrylic acid is 5 to 50 wt % of the total amount of the polymerizable vinyl monomers, and the methyl methacrylate is 50 to 95 wt % of the total amount of the polymerizable vinyl monomers.

* * * * *

UNITED STATES PATENT AND TRADEMARK OFFICE
CERTIFICATE OF CORRECTION

PATENT NO. : 6,967,026 B2
DATED : November 22, 2005
INVENTOR(S) : Noboru Hoshi, Toshio Shimamoto and Shigeru Sugiyama It is certified that error appears in the above-identified patent and that said Letters Patent is hereby corrected as shown below:

<u>Title page,</u>
Item [87], PCT Pub. Date, should read -- Mar. 7, 2002 --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,967,026 B2 |
| APPLICATION NO. | : 10/362114 |
| DATED | : November 22, 2005 |
| INVENTOR(S) | : Noboru Hoshi, Toshio Shimamoto and Shigeru Sugiyama |

It is certified that error appears in the above-identified patent and that said Letters Patent is hereby corrected as shown below:

At Column 15, line 31, after "formula" please add -- [1] --.

At Column 15, line 34, please add -- [in the formula, $R_1$ represents a hydrogen atom or a methyl group, and $R_2$ represents a hydrogen atom or an alkyl group having 1 to 4 carbon atoms] --.

At Column 16, line 10, after "formula" please add -- [1] --.

At Column 16, line 13, please add -- [in the formula, $R_1$ represents a hydrogen atom or a methyl group, and $R_2$ represents a hydrogen atom or an alkyl group having 1 to 4 carbon atoms] --.

Signed and Sealed this

Fifth Day of December, 2006

JON W. DUDAS
*Director of the United States Patent and Trademark Office*